(12) United States Patent
Angel

(10) Patent No.: US 9,320,840 B2
(45) Date of Patent: Apr. 26, 2016

(54) CATHETER VACUUM DRESSING APPARATUS AND METHODS OF USE

(71) Applicant: Luis F. Angel, San Antonio, TX (US)

(72) Inventor: Luis F. Angel, San Antonio, TX (US)

( * ) Notice: Subject to any disclaimer, the term of this patent is extended or adjusted under 35 U.S.C. 154(b) by 202 days.

(21) Appl. No.: 14/032,139

(22) Filed: Sep. 19, 2013

(65) Prior Publication Data

US 2014/0100536 A1  Apr. 10, 2014

Related U.S. Application Data

(60) Provisional application No. 61/710,285, filed on Oct. 5, 2012.

(51) Int. Cl.
| | | |
|---|---|---|
| *A61M 1/00* | (2006.01) | |
| *A61M 25/02* | (2006.01) | |
| *A61F 13/02* | (2006.01) | |

(Continued)

(52) U.S. Cl.
CPC ........ *A61M 1/0088* (2013.01); *A61F 13/00068* (2013.01); *A61F 13/0203* (2013.01); *A61M 25/02* (2013.01); *A61F 13/00063* (2013.01); *A61F 2013/0074* (2013.01); *A61F 2013/00182* (2013.01); *A61F 2013/00412* (2013.01); *A61F 2013/00536* (2013.01); *A61M 1/0031* (2013.01); *A61M 39/0247* (2013.01); *A61M 2025/0246* (2013.01); *A61M 2025/0253* (2013.01); *A61M 2025/0266* (2013.01); *A61M 2025/0273* (2013.01); *A61M 2039/0261* (2013.01)

(58) Field of Classification Search
CPC .......... A61M 1/0088; A61M 39/0247; A61M 27/00; A61M 2039/0261; A61M 2039/0273; A61M 2039/0276; A61M 2039/0279; A61M 2039/0282; A61M 2025/0246; A61M 2025/0253; A61M 2025/0266; A61M 2025/0273; A61M 25/02; A61F 13/00063; A61F 13/00068; A61F 2013/00182; A61F 2013/0074; A61F 2013/00412; A61F 2013/00536; A61F 13/0203
See application file for complete search history.

(56) References Cited

U.S. PATENT DOCUMENTS

| | | | | |
|---|---|---|---|---|
| 4,275,721 | A | * | 6/1981 | Olson .......................... 604/180 |
| 4,941,882 | A | | 7/1990 | Ward et al. .................... 604/180 |
| 5,000,741 | A | | 3/1991 | Kalt .............................. 604/180 |

(Continued)

FOREIGN PATENT DOCUMENTS

| | | | | |
|---|---|---|---|---|
| EP | | 1 863 549 | 3/2006 | ............. A61M 1/00 |
| WO | WO 2008/040020 | | 4/2008 | ............ A61M 27/00 |

(Continued)

OTHER PUBLICATIONS

Eisenhardt, et al., "Negative pressure wound therapy reduces the ischaemia/reperfusion-associated inflammatory response in free muscle flaps" *Journal of Plastic, Reconstructive & Aesthetic Surgery* 65(5): 640-649 (2012).

(Continued)

*Primary Examiner* — Adam Marcetich
(74) *Attorney, Agent, or Firm* — David G. Rosenbaum; J. Peter Paredes; Rosenbaum IP, P.C.

(57) ABSTRACT

A vacuum dressing to cover a medical device insertion site, generally comprising a transparent film dressing member, adapted to form a sealed region between the film dressing member and a region of skin surrounding the insertion site; a sponge/foam member adapted to be positioned over the insertion site; and vacuum tubing, wherein the vacuum tubing permits vacuum pressure to be applied to the sealed region.

13 Claims, 13 Drawing Sheets

(51) Int. Cl.
*A61F 13/00* (2006.01)
*A61M 39/02* (2006.01)

(56) References Cited

U.S. PATENT DOCUMENTS

| | | | | |
|---|---|---|---|---|
| 5,306,256 | A * | 4/1994 | Jose | A61M 25/02 |
| | | | | 128/DIG. 26 |
| 5,370,627 | A * | 12/1994 | Conway | A61M 25/02 |
| | | | | 128/DIG. 26 |
| 5,685,859 | A * | 11/1997 | Kornerup | 604/180 |
| 5,833,665 | A * | 11/1998 | Bootman et al. | 604/180 |
| 6,071,267 | A * | 6/2000 | Zamierowski | 604/289 |
| 6,124,521 | A * | 9/2000 | Roberts | 602/54 |
| 6,203,563 | B1 | 3/2001 | Fernandez | 606/215 |
| 6,638,270 | B2 | 10/2003 | Johnson | 604/890.1 |
| 7,534,240 | B1 | 5/2009 | Johnson | 604/543 |
| 7,723,560 | B2 | 5/2010 | Lockwood et al. | 602/45 |
| 7,988,673 | B2 | 8/2011 | Wright et al. | 604/174 |
| 8,100,862 | B2 | 1/2012 | Bierman | 604/174 |
| 2002/0128605 | A1* | 9/2002 | Miller | A61M 25/02 |
| | | | | 604/172 |
| 2002/0161346 | A1 | 10/2002 | Lockwood et al. | 604/315 |
| 2004/0102736 | A1 | 5/2004 | Bierman | 604/180 |
| 2004/0127863 | A1* | 7/2004 | Bubb et al. | 604/317 |
| 2007/0010778 | A1 | 1/2007 | Burrell et al. | 602/54 |
| 2007/0055205 | A1* | 3/2007 | Wright et al. | 604/174 |
| 2007/0265585 | A1 | 11/2007 | Joshi et al. | 604/313 |
| 2009/0187259 | A1 | 7/2009 | Argenta et al. | 623/23.74 |
| 2009/0264838 | A1* | 10/2009 | Livne et al. | 604/290 |
| 2009/0275922 | A1* | 11/2009 | Coulthard et al. | 604/543 |
| 2010/0106095 | A1* | 4/2010 | Vitaris et al. | 604/177 |
| 2010/0121280 | A1* | 5/2010 | Fleischer | A61M 25/02 |
| | | | | 604/179 |
| 2010/0228183 | A1* | 9/2010 | Sunnen | 604/25 |
| 2010/0268176 | A1 | 10/2010 | Johnson et al. | 604/290 |
| 2011/0060204 | A1 | 3/2011 | Weston | 600/364 |
| 2011/0092927 | A1* | 4/2011 | Wilkes et al. | 604/304 |
| 2011/0184361 | A1 | 7/2011 | Crojzat et al. | 604/319 |
| 2011/0184362 | A1 | 7/2011 | Crojzat et al. | 604/319 |
| 2011/0245788 | A1 | 10/2011 | Marquez Canada | 604/319 |
| 2012/0197204 | A1 | 8/2012 | Helm, Jr. | 604/176 |
| 2012/0203182 | A1* | 8/2012 | Kay | A61L 24/0031 |
| | | | | 604/180 |
| 2012/0253302 | A1 | 10/2012 | Corley | 604/319 |
| 2013/0274667 | A1* | 10/2013 | Conrad-Vlasak et al. | 604/117 |

FOREIGN PATENT DOCUMENTS

| | | | | |
|---|---|---|---|---|
| WO | WO 2009/124548 | | 10/2009 | A61M 1/00 |
| WO | WO 2012/079394 | | 6/2012 | A61M 27/00 |

OTHER PUBLICATIONS

Graeme, et al., "The methodology of negative pressure wound therapy: Separating fact from fiction" *Journal of Plastic, Reconstructive & Aesthetic Surgery* 65(8):989-1001 (2012).

Lee, et al., "intravenous insertion site protection: Moisture accumulation in intravenous site protectors" *J Intraven Nurs.* 19(4): 194-197 (1996).

Moües, et al., "A review of topical negative pressure therapy in wound healing: sufficient evidence?" *The American Journal of Surgery*, 201(4): 544-556 (2011).

Perez, et al., "The use of an abdominal vacuum-dressing system in the management of abdominal wound complications" *Adv Surg.* 41: 121-131 (2007).

Rozen, et al., "An improved alternative to vacuum-assisted closure (VAC) as a negative pressure dressing in lower limb split skin grafting: a clinical trial" *Journal of Plastic, Reconstructive & Aesthetic Surgery* 61(3): 334-337 (2008).

Sciortino, et al., "Case report: treatment of sever subcutaneous emphysema with a negative pressure wound therapy dressing" *Eplasty* 9:e1 (2009).

\* cited by examiner

Figure 1 - Prior Art
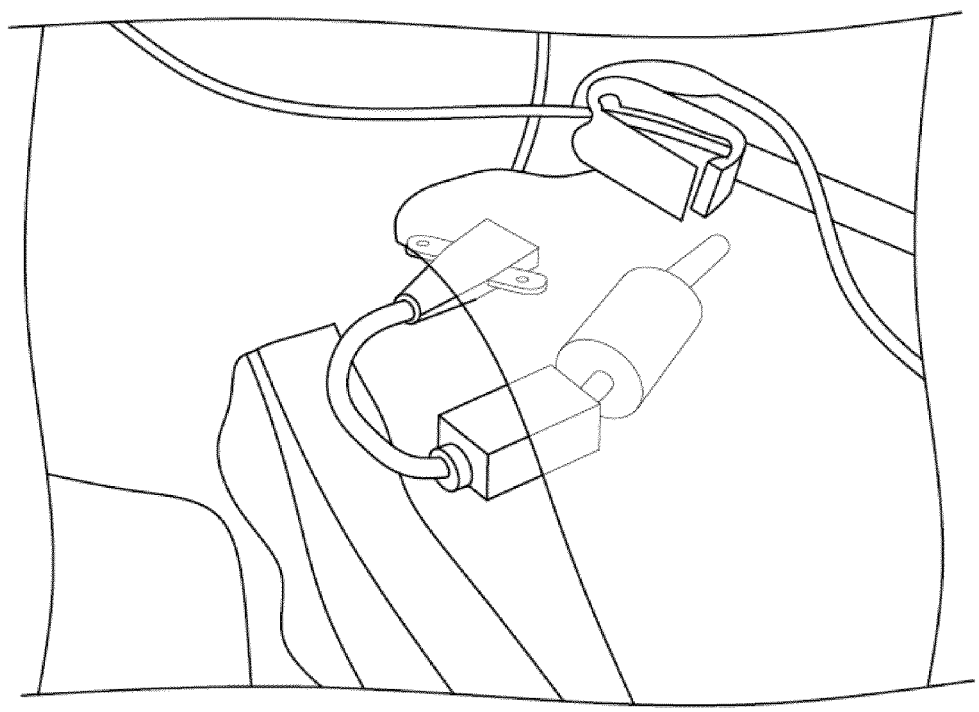

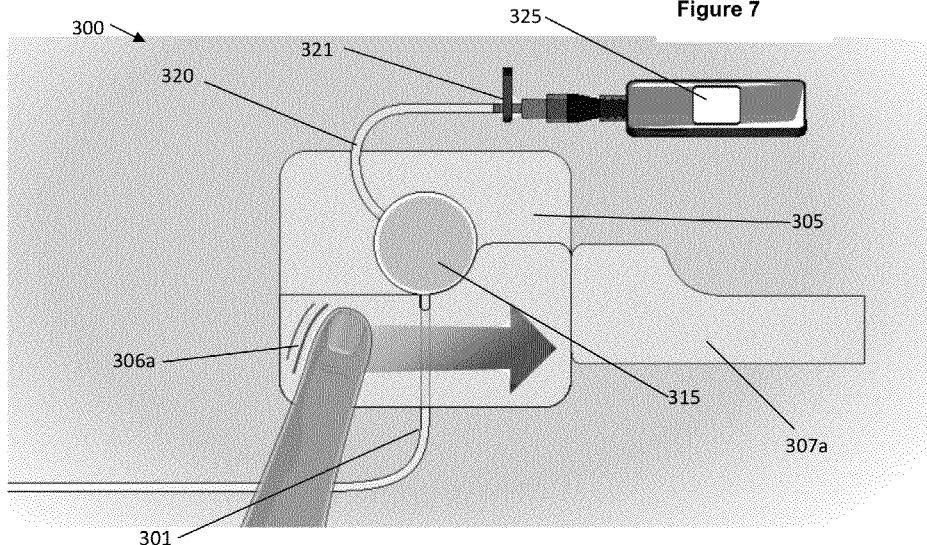
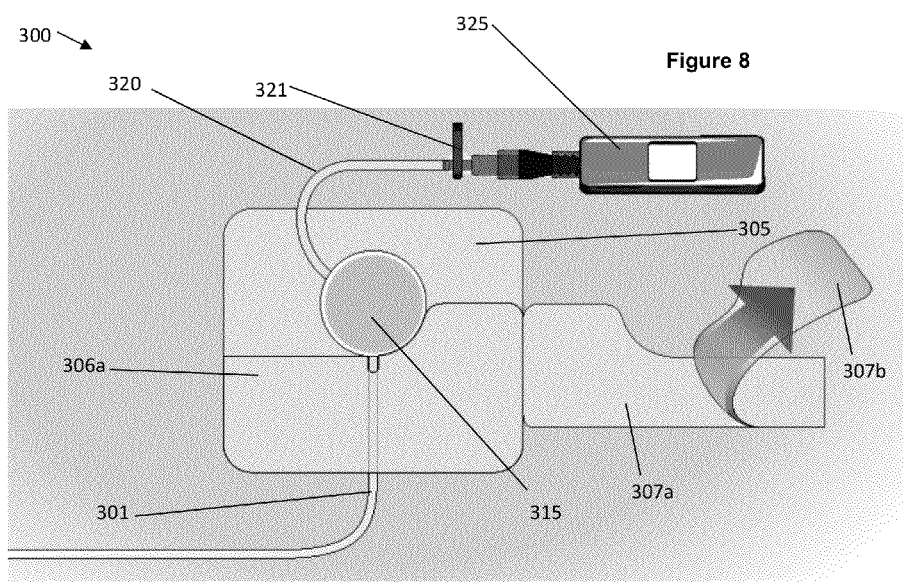

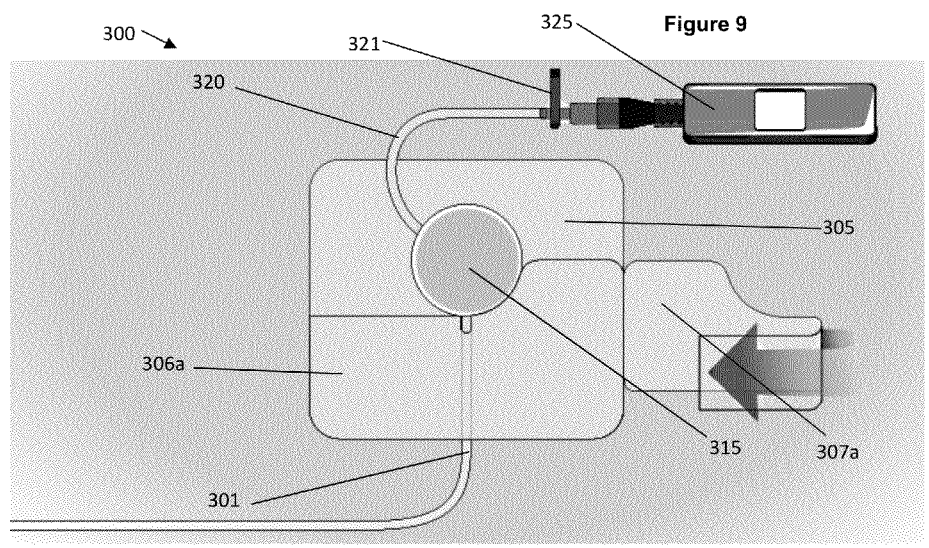
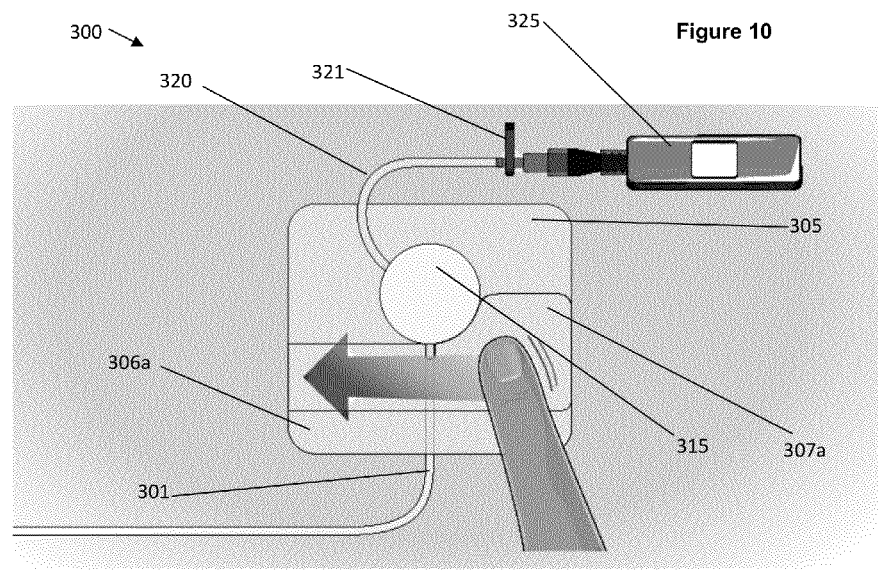

CATHETER VACUUM DRESSING APPARATUS AND METHODS OF USE

CROSS-REFERENCE TO RELATED APPLICATIONS

The present application claims priority to U.S. Provisional Application Ser. No. 61/710,285, filed Oct. 5, 2012, which is hereby incorporated by reference in its entirety.

BACKGROUND

The invention generally relates to wound dressings. More particularly, the invention relates to vacuum dressings for medical device insertion sites.

Transcutaneous medical devices are catheters, pins, implants and the like which pass through the skin and are indwelling for some variable periods of time. Exemplary of transcutaneous medical devices are central venous catheters, peripheral venous catheters, Swan-Ganz pulmonary catheters, central nervous system implants (ex. external ventricular drainage and ventricular reservoirs), peritoneal dialysis catheters, such as for continuous ambulatory peritoneal dialysis and continuous cyclic peritoneal dialysis, hemodialysis catheters, transvenous pacemaker leads, chest drainage tubes and catheters as well as other cavity drainage tubes and temporary orthopedic pins. All of these transcutaneous medical devices, when in place, have a portion of the device which is external, that is which is left protruding from the skin, and which can be the cause of infection.

The risk of acquiring infections from transcutaneous infections is very high. For instance, the risk of acquiring catheter-related bloodstream infection ranges from 0.9 to 8%. These nosocomial bloodstream infections cause a case fatality of more than 20%, and account for an increase of thousands of dollars in hospital costs per infection, or tens of thousands of dollars per survivor in ICU needing an extra week of hospital stay. As for peritoneal dialysis, a very experienced center today still has a peritonitis rate of one episode per 15 to 25 patient months. The major sources of bacteria in these infections are from surrounding skin.

To prevent infections associated with transcutaneous medical devices, universal precautions such as the use of gloves, mask and a cap in combination with the use of antiseptic preparation at the insertion sites, including the initial application of topical anti-microbial solutions such as alcohol, iodine or more recently chlorexedine is known. A further topical ointment after insertion of the device, such as an ointment containing neomycin, polymyxin and bacitracin, has been shown to prevent catheter colonization/infection, but it may increase the risk of fungal infection. Ointments are also inconvenient, requiring multiple replacements. There have also been attempts to attach a cuff to the catheters, with an anti-microbial agent impregnated in the cuff. Efforts to coat the catheters with anti-microbial agents are known. However, none of these efforts has been completely successful in clinical trials. Presently, the most common catheter dressing used in hospitals comprises sterile gauze or polyurethane film, which both have limited infection control properties and are difficult to keep in place particularly in hospitalized patients that are at the highest risk of infection related to these devices.

Current dressings for medical device insertion sites, such as that shown in use in FIG. 1, fail to provide adequate protection to the insertion site, as they require that the medical device be located underneath the dressing. Because of this, any pressure on or movement of the medical device is associated with the dressing not being in contact with the skin, thereby facilitating infections.

The present invention seeks to overcome these problems, as well as others.

SUMMARY OF THE INVENTION

A vacuum dressing to cover a medical device insertion site is disclosed and comprises: a transparent film dressing member, adapted to form a sealed region between the film dressing member and a region of skin surrounding the insertion site; a foam member adapted to be positioned over the insertion site; and a vacuum tubing member, wherein the vacuum tubing member permits vacuum pressure to be applied to the sealed region between the insertion site and the film dressing member; wherein the vacuum dressing is adapted to provide a negative pressure environment over the insertion site and maintain the negative pressure environment despite movements of the medical device.

A method of using a vacuum dressing to cover a medical device insertion site is disclosed and comprises disposing the vacuum dressing over the medical device insertion site, wherein the vacuum dressing comprises a transparent film dressing, a foam member, and vacuum tubing; sealing the transparent film dressing over and around the medical device insertion site; and applying a vacuum force through the vacuum tubing to a region around the medical device insertion site and sealed by the dressing, to obtain a desired vacuum level.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 1 is a depiction of a prior art dressing for a medical device insertion site, in use.

FIG. 7 is an illustration of a fifth step of applying one embodiment of the vacuum dressing.

FIG. 8 is an illustration of a sixth step of applying one embodiment of the vacuum dressing.

FIG. 9 is an illustration of a seventh step of applying one embodiment of the vacuum dressing.

FIG. 10 is an illustration of an eighth step of applying one embodiment of the vacuum dressing.

DETAILED DESCRIPTION OF THE INVENTION

Figure 2A:
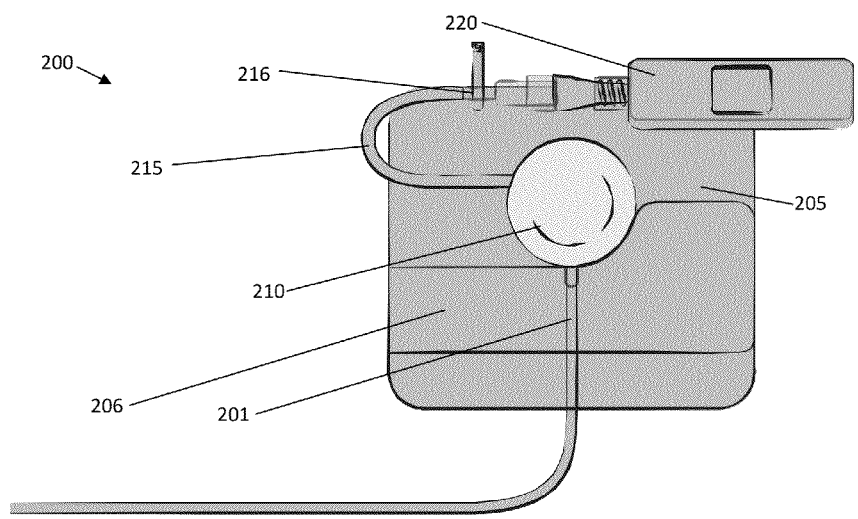
FIG. 2A is a depiction of one embodiment of the vacuum dressing.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Provided herein are apparatuses, systems and methods for a vacuum dressing for medical device insertion sites. The design of the inventive vacuum dressing allows placement over the medical device with no interference for the handling of the device, while at the same time providing a protective covering of the area in which the device is inserted into the skin. The main objective of this design is to decrease the risk of infections associated with medical devices at the entry site in the skin. The vacuum used at the entry site will create a negative pressure environment that will suction any blood or fluids leaking from the medical device insertion site, in a low or no oxygen environment (anaerobic) which will also promote healing around the medical device. The negative pressure environment will also serve to make the migration of infectious agents such as bacteria and fungi more difficult. Having a negative or vacuum pressure foam or other similar material over the catheter will provide significant benefits such as promoting healing at the insertion site, creating a low oxygen or anaerobic environment that will impede the bacterial or fungal growth in the access site, and also the negative or vacuum pressure will promote the fluids and possible infectious agents into the foam or similar material used in the dressing to be accumulated in this part. The foam or material may also have antimicrobial agents that will decrease or eliminate the growth of these infectious agents.

In one embodiment, the vacuum dressing of the present invention comprises: a dressing member having a slit for disposing a portion of the medical device therethrough, a first flap which is adapted to fold over the slit and beneath the portion of the medical device disposed through the slit, and a second flap which is adapted to fold over the first flap and over the medical device; a foam/sponge member coupled to the dressing member, positioned so as to sit over the medical device insertion site; and vacuum tubing in operative communication with a region between the skin surrounding the medical device insertion site and the dressing member, said vacuum tubing adapted to be coupled to a vacuum source. In many embodiments the dressing member is adhesive on a side adapted to be applied to a region of skin surrounding the medical device insertion site. In some embodiments, the flaps may have an adhesive side adapted to be applied to either the base dressing or the other flap. Preferably, the flaps form a moveable flap portion for the catheter for free range of movement of the catheter without breaking the vacuum seal.

In use, once the vacuum dressing is applied, a vacuum force is applied to the region between the skin surrounding the medical device insertion site and the dressing member via a vacuum source coupled to the vacuum tubing, creating a negative pressure environment in said region. This negative pressure environment suctions any blood or fluids leaking from the medical device insertion site, in a low or no oxygen environment (anaerobic), which will also promote healing around the medical device. The negative pressure environment will also serve to make the migration of infectious agents such as bacteria and fungi more difficult. As the negative pressure environment is created, the foam/sponge will compress, indicating a successful vacuum level/negative pressure environment is forming. Because of this deformation of the foam/sponge, it is possible to easily confirm the status/integrity of the applied dressing by visual observation. In use, once a desired vacuum level is achieved, the vacuum source may be disconnected from the vacuum tubing and the tubing sealed. The combination of the negative pressure and the release of the catheter from underneath the dressing to the area where it is fixated to the skin and above the dressing with a series of overlying dressings maintain the integrity of the dressing and the vacuum.

If it is observed that the dressing is not maintaining a negative pressure environment, such as through an absence of deformation of the foam/sponge, the vacuum force should be reapplied to renew the negative pressure environment. If the negative pressure environment cannot be reobtained, then the vacuum dressing should be removed and a new dressing applied.

In some embodiments, a preferred vacuum pressure for the negative pressure environment is between about 50 and about 175 mmHg. In some embodiments, the vacuum pressure is a level below normal atmospheric pressure.

In some alternative embodiments, at least one oxygen sensor may be coupled with the vacuum dressing and/or the foam/sponge member, to provide electronic monitoring of the status of the negative pressure environment. In further alternative embodiments, at least one pressure sensor may be coupled to the vacuum dressing, adapted to detect decreased pressure of the dressing in contact with the skin, which would indicate that the dressing is separating from the skin. The pressure sensor(s) may detect levels of vacuum pressure below ideal pressure levels of between about 50 and about 175 mmHg.

Examples of medical devices include, but are not limited to, catheters, tubes, or other devices.

In a preferred embodiment, the dressing member is a transparent film dressing, such as Tegaderm®. In many embodiments the dressing member is adhesive.

In some embodiments, the vacuum source is a syringe. In further embodiments, the vacuum source may be a mechanical non-electronic system that can apply and maintain a negative pressure. In some embodiments, the vacuum source is a vacuum pump device.

In some embodiments, the foam/sponge is round or oval in shape, to optimize sealing ability over the insertion site. In other embodiments, the foam/sponge may have any desired shape or size sufficient to provide a seal over the insertion site of the medical device. In some embodiments, the foam/sponge may further comprise at least one of a bacteriostatic, antiseptic, or antibiotic agent. In some embodiments, the foam/sponge may be used without antiseptic or antibiotic.

In another embodiment, the second flap of the dressing member may have a non-adhesive region positioned to sit over the medical device. This non-adhesive region helps prevent movement of the medical device from causing unwanted movement of the dressing, preserving the integrity of the applied dressing.

In another embodiment, the vacuum dressing is adapted to have the first and second flaps not adhered to the dressing body member, so as to permit the disposed portion of the medical device to move without displacing the dressing from the skin surrounding the medical device insertion site.

In a particular embodiment, the medical device is a catheter. In this embodiment, the vacuum dressing comprises: a dressing member having a slit for disposing a portion of the catheter therethrough, a first flap which is adapted to fold over the slit and beneath the portion of the catheter disposed through the slit, and a second flap which is adapted to fold over the first flap and over the catheter; a foam/sponge member coupled to the dressing member, positioned so as to sit over the catheter insertion site; and vacuum tubing in operative communication with a region between the skin surrounding the catheter insertion site and the dressing member, said vacuum tubing adapted to be coupled to a vacuum source.

In one embodiment, there is disclosed a vacuum dressing system for covering a medical device insertion site, comprising: a sponge/foam member for placement in contact with the insertion site; a transparent film dressing member, adapted to form a vacuum seal between the film dressing member and a region of skin surrounding the insertion site; a vacuum pressure source; and vacuum tubing, wherein the vacuum tubing permits vacuum pressure to be applied by the vacuum pressure source to the sealed region between the insertion site and the film dressing member.

In one embodiment, disclosed is a method of using the inventive vacuum dressing to cover a medical device insertion site, comprising the steps of: disposing the vacuum dressing over the medical device insertion site; sealing the dressing over the medical device insertion site; and applying a vacuum force through vacuum tubing to the medical device insertion site, to obtain a desired vacuum level. In some embodiments, the vacuum dressing comprises a sponge material, vacuum tubing, and a transparent film dressing.

In some embodiments, the method further comprises the step of applying vacuum force to create an area of negative pressure around the medical device insertion site resulting in an anaerobic environment that inhibits the growth of infectious agents.

In some embodiments, the method further comprises the step wherein a maintained vacuum level confirms that the dressing is providing anaerobic conditions and does not need to be changed.

In some embodiments, the method further comprises the step wherein a loss of vacuum level indicates a need to reapply the vacuum force.

In some embodiments, the method further comprises the step wherein failure to obtain the vacuum level by reapplying the vacuum force indicates a need to replace the dressing.

In another embodiment, there is disclosed a vacuum dressing system for covering a medical device insertion site, comprising: a base transparent film dressing member, adapted to form a vacuum seal between the film dressing member and a region of skin surrounding the insertion site; a vacuum pressure source; a sponge/foam member for placement in contact with the insertion site; and vacuum tubing, wherein the vacuum tubing permits vacuum pressure to be applied by the vacuum pressure source to the sealed region between the insertion site and the film dressing member. The vacuum dressing of this embodiment provides a flexible region for movement of a portion of a medical device without disturbing a negative pressure environment established over the insertion site of the medical device.

The design of the invention further allows users to obtain objective evidence that the dressing is working Currently available dressings do not provide a way to evaluate the integrity of the dressing different than the observation over the catheter. However, with this invention the visual confirmation of a negative pressure environment over the dressing, the ability to keep negative pressure or a visual confirmation with color or other means that indicate the negative pressure environment is present and will allow the patient or personnel taking care of the patient to recognize that the dressing is not covering the insertion point adequately and may need to be replaced.

FIG. 2A depicts an embodiment of the vacuum dressing 200 of the present invention, comprising: a dressing member 205 having a slit for disposing a portion of the medical device 201 therethrough, a first flap 206 which is adapted to fold over the slit and above or beneath the portion of the medical device 201 disposed through the slit; a foam/sponge member 210 coupled to the dressing member 205, positioned so as to sit over the medical device 201 insertion site; and vacuum tubing 215 in operative communication with a region between the skin surrounding the medical device 201 insertion site and the dressing member 205, said vacuum tubing 215 adapted to be coupled to a vacuum source 220. In some embodiments, the vacuum tubing 215 is coupled to a vacuum source 220 at a sealable valve 216, which permits applied vacuum pressure to be maintained after the vacuum source 220 is detached from the vacuum tubing 215.

Figure 2B:
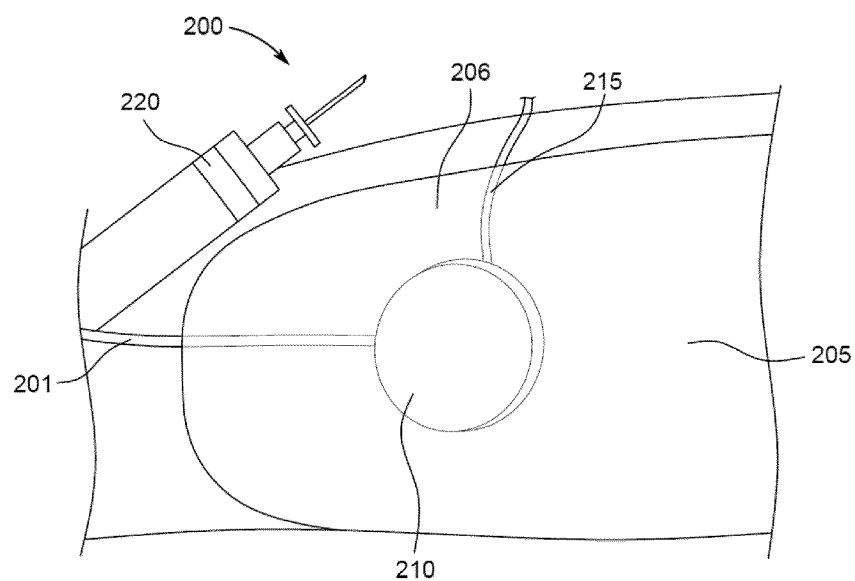
FIG. 2B is a depiction of an embodiment of the vacuum dressing in use.

FIG. 2B depicts an embodiment of the vacuum dressing 200 of the present invention in use, the dressing comprising: a dressing member 205 having a slit for disposing a portion of the medical device 201 therethrough, a first flap 206 which is adapted to fold over the slit and beneath the portion of the medical device 201 disposed through the slit; a foam/sponge member 210 coupled to the dressing member 205, positioned so as to sit over the medical device 201 insertion site; and vacuum tubing 215 in operative communication with a region between the skin surrounding the medical device 201 insertion site and the dressing member 205, said vacuum tubing 215 adapted to be coupled to a vacuum source 220. In one embodiment, the foam/sponge member may be round, elliptical, oblong, polygonal, pentagonal, hexagonal, or size or shape as properly seal an insertion point.

Examples of medical devices 201 include, but are not limited to, catheters, tubes, pacemakers, diabetic delivery systems, drug delivery systems, or other devices.

In a preferred embodiment, the dressing member 205 is a transparent film dressing, such as Tegaderm®. In many embodiments the dressing member 205 is adhesive on a side adapted to be applied to a region of skin surrounding the medical device insertion site. In some embodiments, the flap 206 may have an adhesive side adapted to be applied to the base dressing 205. Alternatively, the dressing member 205 includes a side of electrostatic charge, such that the electrostatic charge adheres or is drawn to the skin. Alternatively, the dressing member 205 includes any adhesive material, typically liquid or semi-liquid, that adheres or bonds items together. The adhesive material may be a natural or synthetic material. The adhesive material may be cured (hardened) by either evaporating a solvent or by chemical reactions that occur between two or more constituents.

In some embodiments, the vacuum source 220 is a syringe. In further embodiments, the vacuum source 220 may be a mechanical non electronic system that can apply and maintain a negative pressure. In some embodiments, the vacuum source 220 is a vacuum pump device.

In some embodiments, the foam/sponge 210 is round or oval in shape, to optimize sealing ability over the insertion site. In other embodiments, the foam/sponge 210 may have any desired shape or size sufficient to provide a seal over the insertion site of the medical device 201. In some embodiments, the foam/sponge 210 may further comprise at least one of a bacteriostatic, antiseptic, or antibiotic agent. In some embodiments, the foam/sponge 210 may be used without antiseptic or antibiotic.

In another embodiment, the vacuum dressing 200 may be adapted to have the flap 206 not fully adhered to the dressing body member 205, so as to permit the disposed portion of the medical device 201 to move without displacing the dressing 200 from the skin surrounding the medical device insertion site. In another embodiment, the flap 206 of the dressing member 205 may have a non-adhesive region positioned to sit over the medical device 201. This non-adhesive region helps prevent movement of the medical device 201 from causing unwanted movement of the dressing 200, preserving the integrity of the applied dressing.

In a particular embodiment, the medical device is a catheter. In this embodiment, the vacuum dressing comprises: a dressing member having a slit for disposing a portion of the catheter therethrough and a first flap which is adapted to fold over the slit and above or beneath the portion of the catheter disposed through the slit; a foam/sponge member coupled to the dressing member, positioned so as to sit over the catheter insertion site; and vacuum tubing in operative communication with a region between the skin surrounding the catheter insertion site and the dressing member, said vacuum tubing adapted to be coupled to a vacuum source.

In one embodiment, there is disclosed a vacuum dressing system for covering a medical device insertion site, comprising: a sponge/foam member for placement in contact with the insertion site; a transparent film dressing member, adapted to form a vacuum seal between the film dressing member and a region of skin surrounding the insertion site; a vacuum pressure source; and vacuum tubing, wherein the vacuum tubing permits vacuum pressure to be applied by the vacuum pressure source to the sealed region between the insertion site and the film dressing member.

In some embodiments, a preferred vacuum pressure for the negative pressure environment is between about 50 and about 175 mmHg. In some embodiments, the vacuum pressure is a level below normal atmospheric pressure.

In some alternative embodiments, an oxygen sensor may be coupled with the vacuum dressing 200 and/or the foam/sponge member 210, to provide electronic monitoring of the status of the negative pressure environment. In further alternative embodiments, a pressure sensor may be coupled to the vacuum dressing 200, adapted to detect decreased pressure of the dressing 205 in contact with the skin, which would indicate that the dressing 205 is separating from the skin. The pressure sensor may detect levels of vacuum pressure below ideal pressure levels of between about 50 and about 175 mmHg.

Figure 3:
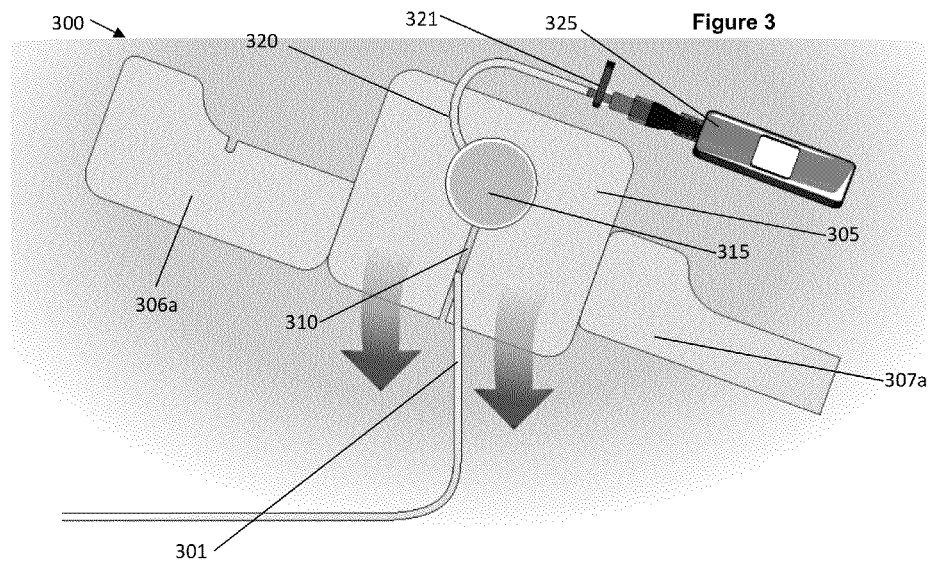
FIG. 3 is an illustration of a first step of applying one embodiment of the vacuum dressing.

As illustrated in FIG. 3, in one embodiment the vacuum dressing 300 of the present invention comprises: a dressing member 305 having a slit 310 for disposing a portion of the medical device 301 therethrough, a first flap 306a which is adapted to fold over the slit 310 and beneath the portion of the medical device 301 disposed through the slit 310, and a second flap 307a which is adapted to fold over the first flap 306a and over the medical device 301; a foam/sponge member 315 coupled to the dressing member 305, positioned so as to sit over the medical device 301 insertion site; and vacuum tubing 320 in operative communication with a region between the skin surrounding the medical device 301 insertion site and the dressing member 305, said vacuum tubing 320 adapted to be coupled to a vacuum source 325. In some embodiments, the vacuum tubing 320 is coupled to a vacuum source 325 at a sealable valve 321, which permits applied vacuum pressure to be maintained after the vacuum source 325 is detached from the vacuum tubing 320.

Examples of medical devices 301 include, but are not limited to, catheters, tubes, or other devices.

In a preferred embodiment, the dressing member 305 is a transparent film dressing, such as Tegaderm ®. In many embodiments the dressing member 305 is adhesive on a side adapted to be applied to a region of skin surrounding the medical device insertion site. In some embodiments, the flaps 306a, 307a may have an adhesive side adapted to be applied to either the base dressing 305 or the other flap 306a, 307a.

In some embodiments, the vacuum source 325 is a syringe. In further embodiments, the vacuum source 325 may be a mechanical non electronic system that can apply and maintain a negative pressure. In some embodiments, the vacuum source 325 is an electronic vacuum pump device.

In some embodiments, the foam/sponge 315 is round or oval in shape, to optimize sealing ability over the insertion site. In other embodiments, the foam/sponge 315 may have any desired shape or size sufficient to provide a seal over the insertion site of the medical device 301. In some embodiments, the foam/sponge 315 may further comprise at least one of a bacteriostatic, antiseptic, or antibiotic agent. In some embodiments, the foam/sponge 315 may be used without antiseptic or antibiotic.

In another embodiment, the second flap 307a of the dressing member 305 may have a non-adhesive region positioned to sit over the medical device 301. This non-adhesive region helps prevent movement of the medical device 301 from causing unwanted movement of the dressing 300, preserving the integrity of the applied dressing 300.

In another embodiment, the vacuum dressing 300 is adapted to have the first and/or second flaps 306a, 307a not fully adhered to the dressing body member 305, so as to permit the disposed portion of the medical device 301 to move without displacing the dressing 300 from the skin surrounding the medical device insertion site.

In a particular embodiment, the medical device 301 is a catheter. In this embodiment, the vacuum dressing 300 comprises: a dressing member 305 having a slit 310 for disposing a portion of the catheter therethrough, a first flap 306a which is adapted to fold over the slit 310 and beneath the portion of the catheter disposed through the slit 310, and a second flap 307*a* which is adapted to fold over the first flap 306*a* and over the catheter; a foam/sponge member 315 coupled to the dressing member 305, positioned so as to sit over the catheter insertion site; and vacuum tubing 320 in operative communication with a region between the skin surrounding the catheter insertion site and the dressing member 305, said vacuum tubing 320 adapted to be coupled to a vacuum source 325.

FIG. 3 also illustrates a first step in applying the vacuum dressing 300, wherein a portion of the medical device 301 is disposed through the slit 310 in the dressing member 305, such that the foam/sponge member 315 is positioned over the medical device 301 insertion site.

Figure 4:
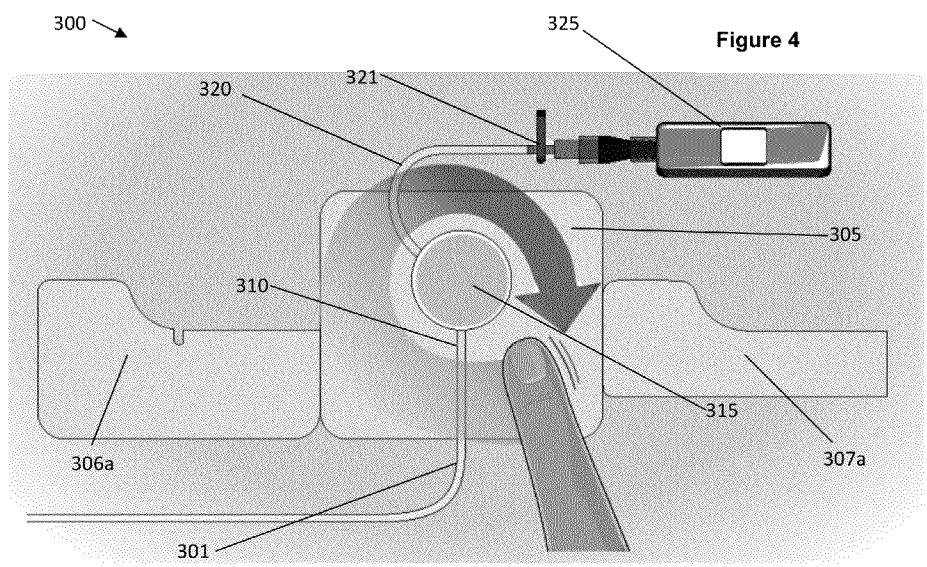
FIG. 4 is an illustration of a second step of applying one embodiment of the vacuum dressing.

FIG. 4 illustrates a second step in applying the vacuum dressing 300, wherein the dressing member 305 is adhered to the skin surrounding the medical device 301 insertion site, so as to enable an applied vacuum force to create an environment of negative pressure between the skin and the vacuum dressing 300.

Figure 5:
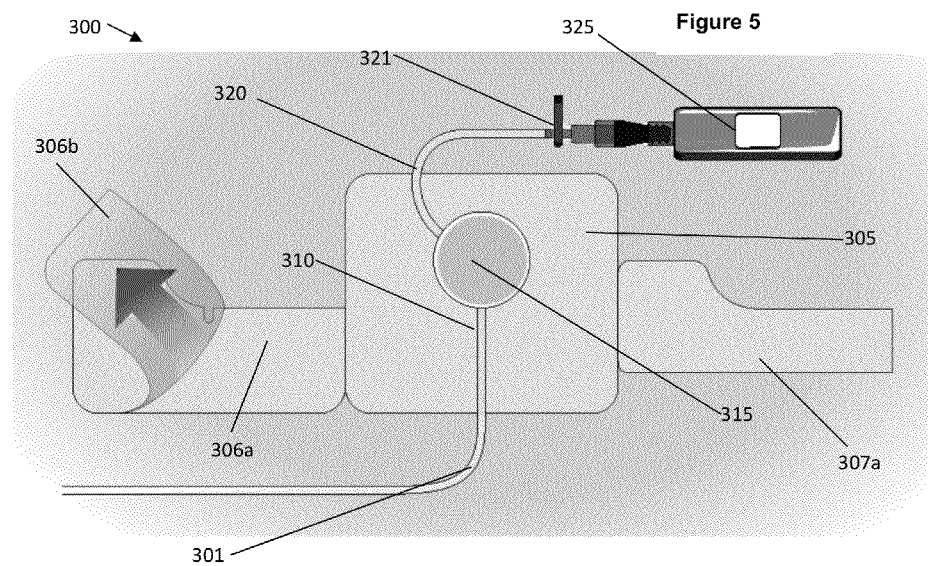
FIG. 5 is an illustration of a third step of applying one embodiment of the vacuum dressing.
Figure 6:
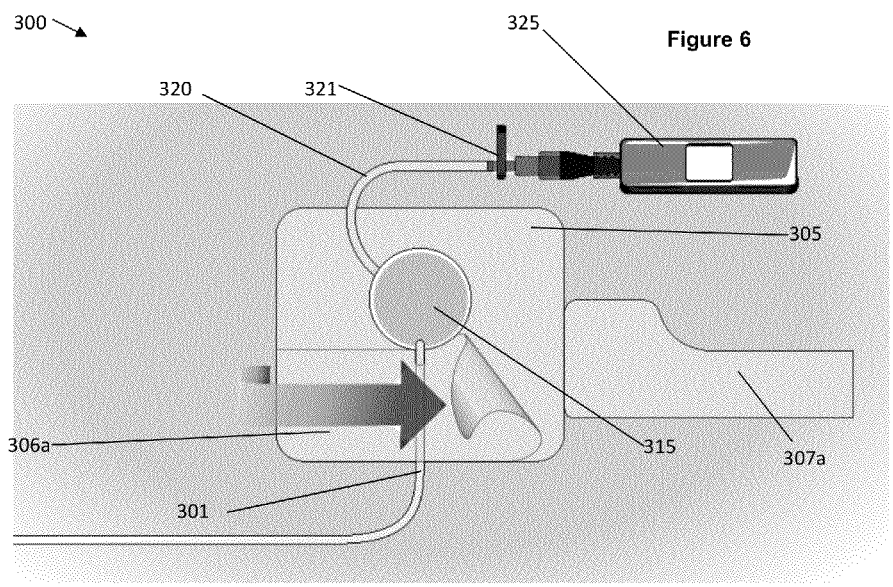
FIG. 6 is an illustration of a fourth step of applying one embodiment of the vacuum dressing.

FIGS. 5-7 illustrate third through fifth steps in applying the vacuum dressing 300, wherein an adhesive portion of the first flap 306*a* is prepared (FIG. 5) by removing a backing 306*b* from the adhesive portion, and then positioned over the slit 310 of the dressing member 305 but beneath the portion of the medical device 301 (FIG. 6), and then the first flap 306*a* is pressed into adhesion with the base dressing member 305 (FIG. 7). The first flap 306*a* provides a seal over the slit 310, such that a negative pressure environment may be formed between the vacuum dressing 300 and the skin surrounding the medical device 301 insertion site.

FIGS. 8-10 illustrate sixth through eighth steps in applying the vacuum dressing 300, wherein an adhesive portion of the second flap 307*a* is prepared (FIG. 8) by removing a backing 307*b* from the adhesive portion, and then positioned over the first flap 306*a* as well as over the portion of the medical device 301 (FIG. 9), and then the second flap 307*a* is pressed into adhesion with the first flap 306*a* (FIG. 10). In some embodiments, the second flap 307*a* has a non-adhesive portion without an adhesive material, such that the non-adhesive portion is positioned over the portion of the medical device 301 above the first flap 306*a*. This non-adhesive region helps prevent movement of the medical device 301 from causing unwanted movement of the dressing 300, preserving the integrity of the applied dressing 300.

Figure 11:
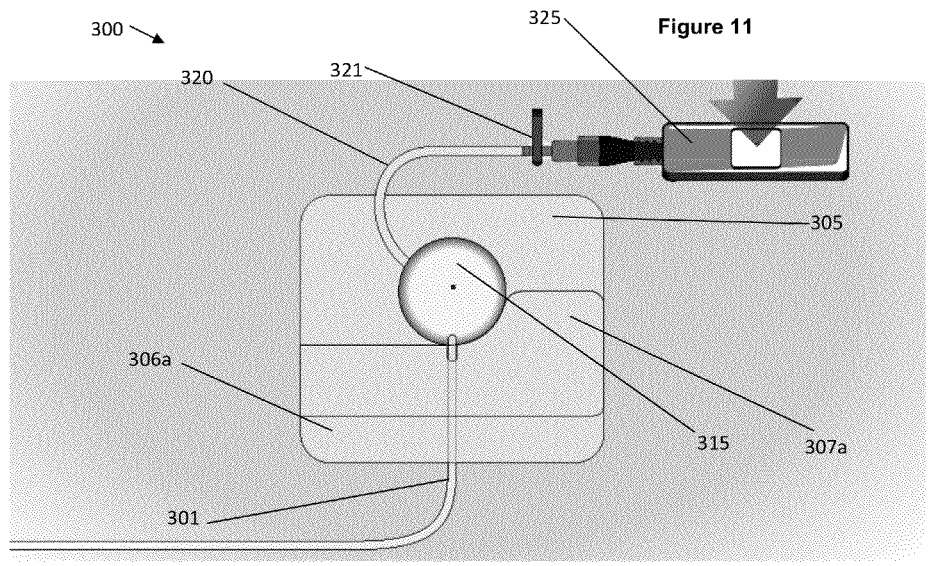
FIG. 11 is an illustration of a ninth step of applying one embodiment of the vacuum dressing.

FIG. 11 illustrates a ninth step in applying the vacuum dressing 300, wherein a vacuum force is applied by a vacuum source 325, via the vacuum tubing 320. The vacuum force is applied to the foam/sponge member 315 and the region between the dressing 300 and the skin surrounding the medical device insertion site.

Figure 12:
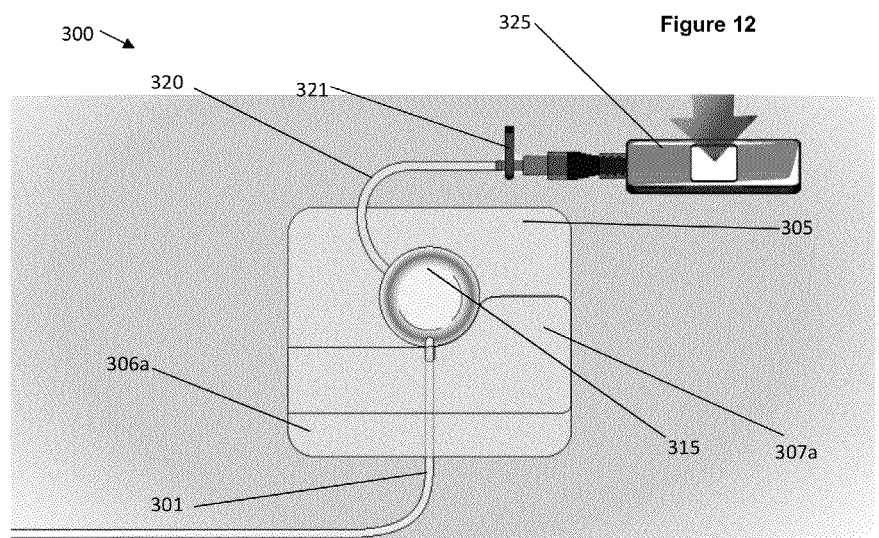
FIG. 12 is an illustration of a tenth step of applying one embodiment of the vacuum dressing.

FIG. 12 illustrates a tenth step in applying the vacuum dressing 300, wherein a negative pressure environment has been created in the region between the dressing 300 and the skin surrounding the medical device insertion site. While the negative pressure environment is applied, the foam/sponge member 315 may be deformed (or compressed), to indicate that the negative pressure environment is maintained. If the negative pressure environment is lost, the foam/sponge member 315 will no longer be deformed or compressed, and return entirely or partially to its original shape/size. When the lack of deformation/compression of the foam/sponge member 315 is observed, indicating that the dressing is not maintaining a negative pressure environment, the vacuum force should be reapplied by the vacuum source 325 to attempt to renew the negative pressure environment. If the negative pressure environment cannot be restored, then the vacuum dressing 300 should be removed and a new dressing 300 applied.

In some embodiments, a preferred vacuum pressure for the negative pressure environment is between about 50 and about 175 mmHg. In some embodiments, the vacuum pressure is a level below normal atmospheric pressure.

In some alternative embodiments, an oxygen sensor (not shown) may be coupled with the vacuum dressing 300 and/or the foam/sponge member 315, to provide electronic monitoring of the status of the negative pressure environment. In further alternative embodiments, a pressure sensor (not shown) may be coupled to the vacuum dressing 300, adapted to detect decreased pressure of the dressing 305 in contact with the skin, which would indicate that the dressing 305 is separating from the skin. The pressure sensor may detect levels of vacuum pressure below ideal pressure levels of between about 50 and about 175 mmHg.

Figure 13:
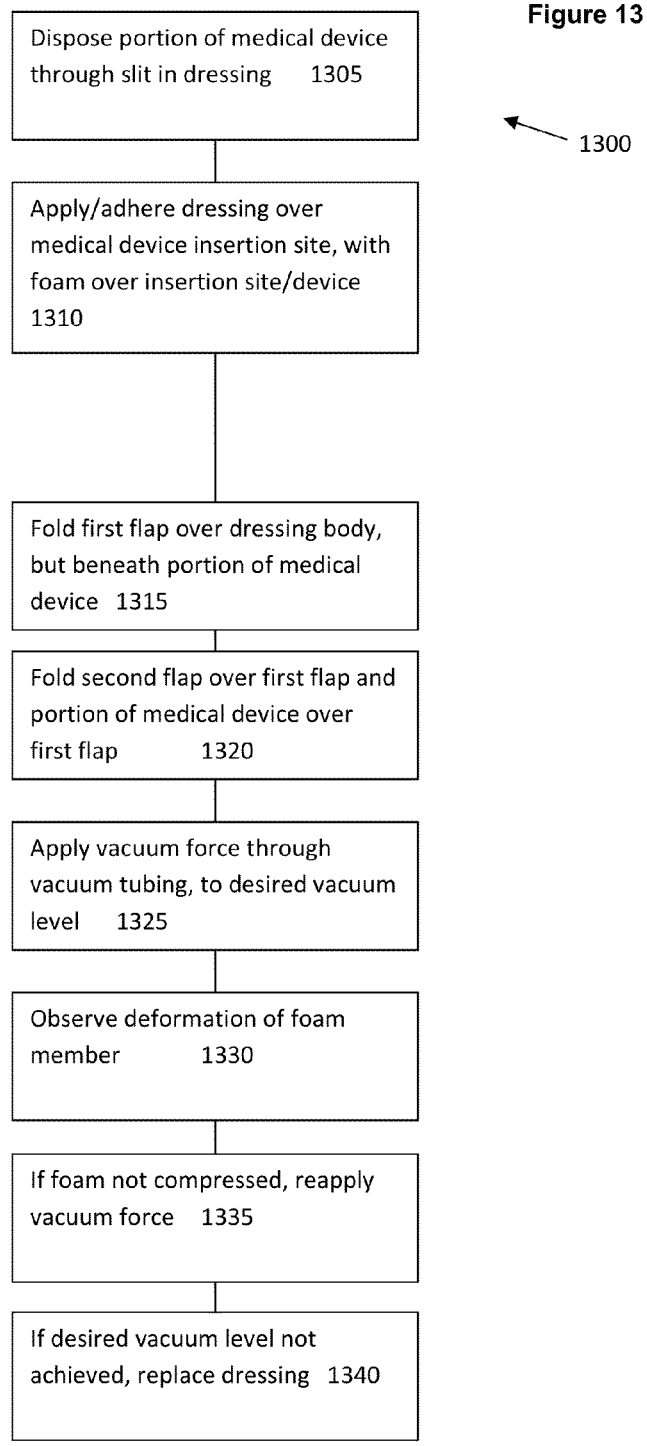
FIG. 13 is a block diagram depicting one embodiment of the method of using the inventive vacuum dressing.

FIG. 13 is a block diagram illustrating a method 1300 of using the inventive vacuum dressing. First (1305), the vacuum dressing is positioned over a medical device insertion site, with at least a portion of the medical device disposed through a slit in the dressing. Next (1310), the dressing is applied/adhered to the skin surrounding the medical device insertion site, with a foam/sponge member (which is coupled to the dressing) positioned over the insertion site. Then (1315), a first flap of the dressing is folded over the dressing body, but beneath the portion of the medical device passing through the slit in the dressing. The first flap is adhered to the dressing body, providing a sealing layer over the slit in the dressing, such that a negative pressure environment can be formed between the skin and the dressing. A second flap is then folded over the first flap (1320), also covering the portion of the medical device disposed above the first flap. In some embodiments, the second flap may have a non-adhesive region positioned to align with the portion of the medical device. This non-adhesive region helps prevent movement of the medical device from displacing the dressing, thereby disturbing an existing negative pressure environment. Once the flaps are applied to the base dressing, a vacuum force is applied through vacuum tubing, until a desired vacuum level is reached (1325). The vacuum force is applied by a vacuum source, such as a syringe or vacuum pump. The vacuum force will create a negative pressure environment in the region between the dressing and the skin surrounding the medical device insertion site. This negative pressure environment suctions any blood or fluids leaking from the medical device insertion site, and forms a low or no oxygen environment (anaerobic) which will also promote healing around the medical device. The negative pressure will also serve to make the migration of infectious agents such as bacteria and fungi more difficult. As the negative pressure environment is created, the foam/sponge may compress, indicating a successful vacuum level/negative pressure environment is forming. Because of this deformation of the foam/sponge, it is possible to easily confirm the status/integrity of the applied dressing by visual observation (1330). In use, once a desired vacuum level is achieved, the vacuum source may be disconnected from the vacuum tubing and the tubing sealed. If it is observed that the dressing is not maintaining a negative pressure environment (1335), such as through an absence of deformation of the foam/sponge member, the vacuum force should be reapplied to renew the negative pressure environment. If the negative pressure environment cannot be reobtained (1340), then the vacuum dressing should be removed and a new dressing applied.

In some embodiments, a preferred vacuum pressure for the negative pressure environment is between about 50 and about 175 mmHg. In some embodiments, the vacuum pressure is a level below normal atmospheric pressure.

In some alternative embodiments, an oxygen sensor may be coupled with the vacuum dressing and/or the foam/sponge member, to provide electronic monitoring of the status of the negative pressure environment. In further alternative embodiments, a pressure sensor may be coupled to the vacuum dressing, adapted to detect decreased pressure of the dressing in contact with the skin, which would indicate that the dressing is separating from the skin. The pressure sensor may detect levels of vacuum pressure below ideal pressure levels of between about 50 and about 175 mmHg.

In one embodiment, disclosed is a method of using the inventive vacuum dressing to cover a medical device insertion site, comprising the steps of: disposing the vacuum dressing over the medical device insertion site; sealing the dressing over the medical device insertion site; and applying a vacuum force through vacuum tubing to the medical device insertion site, to obtain a desired vacuum level. In some embodiments, the vacuum dressing comprises a sponge material, vacuum tubing, and a transparent film dressing.

In some embodiments, the method further comprises the step of applying vacuum force to create an area of negative pressure around the medical device insertion site resulting in an anaerobic environment that inhibits the growth of infectious agents.

In some embodiments, the method further comprises the step wherein a maintained vacuum level confirms that the dressing is providing anaerobic conditions and does not need to be changed.

In some embodiments, the method further comprises the step wherein a loss of vacuum level indicates a need to reapply the vacuum force.

In some embodiments, the method further comprises the step wherein failure to obtain the vacuum level by reapplying the vacuum force indicates a need to replace the dressing.

Examples of medical devices include, but are not limited to, catheters, tubes, or other devices.

In a preferred embodiment, the dressing member is a transparent film dressing, such as Tegaderm®. In many embodiments the dressing member is adhesive.

In some embodiments, the vacuum source is a syringe. In further embodiments, the vacuum source may be a mechanical non electronic system that can apply and maintain a negative pressure. In some embodiments, the vacuum source is a vacuum pump device.

In some embodiments, the foam/sponge is round or oval in shape, to optimize sealing ability over the insertion site. In other embodiments, the foam/sponge may have any desired shape or size sufficient to provide a seal over the insertion site of the medical device. In some embodiments, the foam/sponge may further comprise at least one of a bacteriostatic, antiseptic, or antibiotic agent. In some embodiments, the foam/sponge may be used without antiseptic or antibiotic.

In another embodiment, the second flap of the dressing member may have a non-adhesive region positioned to sit over the medical device. This non-adhesive region helps prevent movement of the medical device from causing unwanted movement of the dressing, preserving the integrity of the applied dressing.

In another embodiment, the vacuum dressing is adapted to have the first and second flaps not adhered to the dressing body member, so as to permit the disposed portion of the medical device to move without displacing the dressing from the skin surrounding the medical device insertion site.

Figure 14:
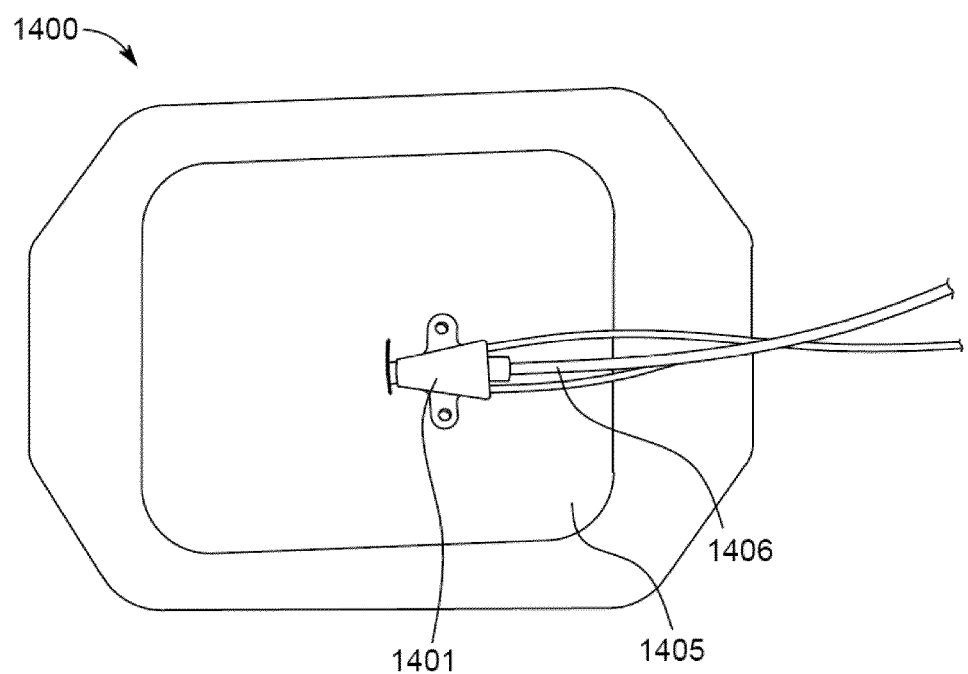
FIG. 14 is an illustration of a partial application of an alternative embodiment of the vacuum dressing, where the vacuum dressing provides a flexible region for movement of a portion of a medical device without disturbing an established negative pressure environment over the insertion site of the medical device.
Figure 15:
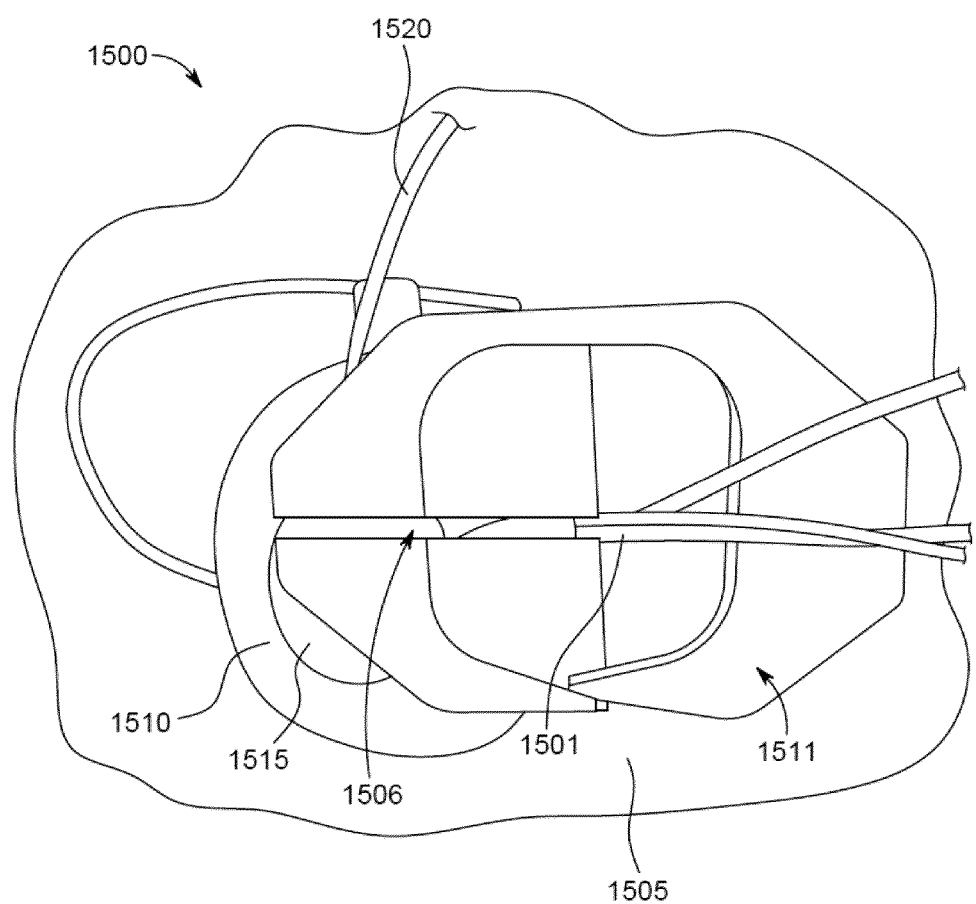
FIG. 15 is an illustration of an alternative embodiment of the vacuum dressing, partially applied, where the vacuum dressing provides a flexible region for movement of a portion of a medical device without disturbing an established negative pressure environment over the insertion site of the medical device.

FIGS. 14-15 depict one manner of preparing a flexible portion of the dressing, so as to permit the disposed portion of the medical device to move without displacing the dressing from the skin surrounding the medical device insertion site. A portion of a medical device 1401, for example a portion of a central venous catheter, is disposed through a slit 1406 in a base section of dressing material 1405.

As illustrated in the applied dressing 1500 of FIG. 15, the portion of the medical device 1501 is disposed over the base dressing layer 1505 and beneath the top dressing layer 1510. The dressing 1500 further comprises a foam/sponge member 1515 and vacuum tubing 1520. In some embodiments, at least one section of dressing material may include a slit 1506 for disposing a portion of the medical device 1501 therethrough. As shown in FIG. 15, an additional section of dressing material 1511 may be applied to provide a flexible region that permits movement of a portion of the medical device 1501 without disrupting a negative pressure environment formed over the insertion site between the dressing 1500 and a patient's skin.

Figure 16:
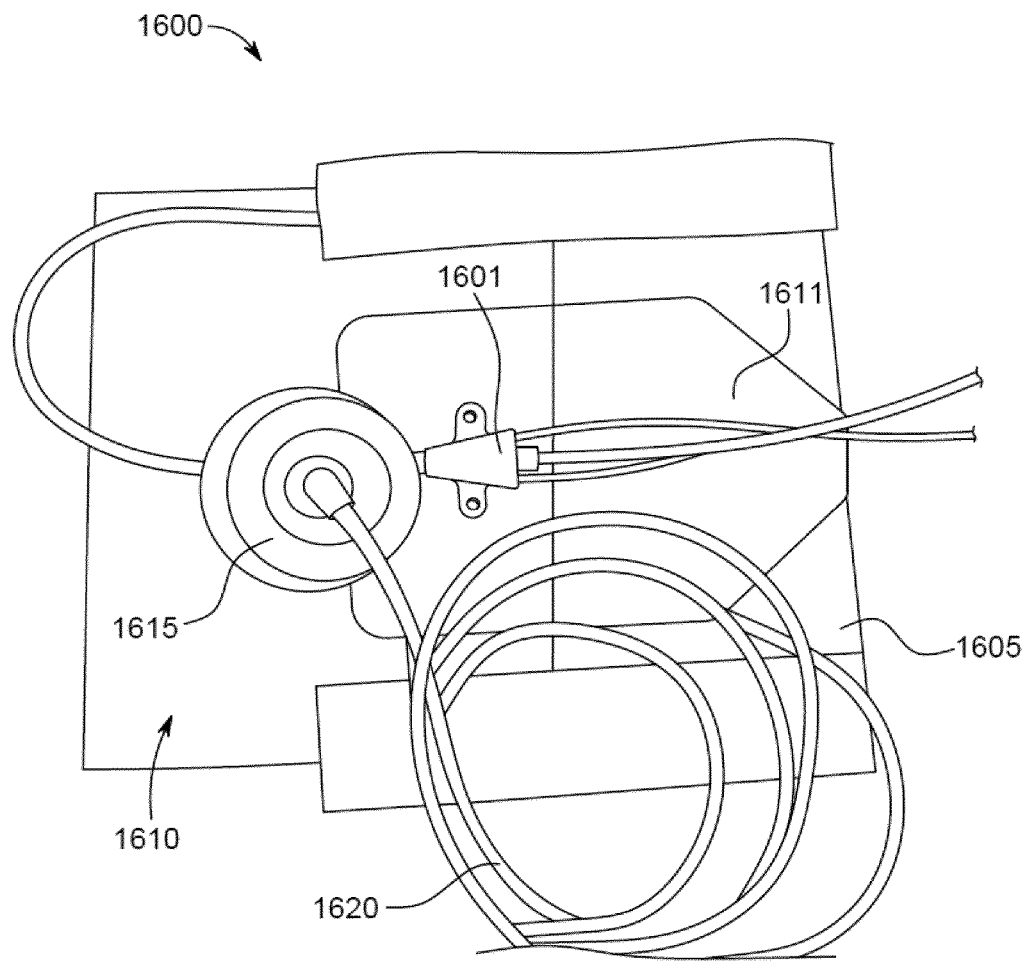
FIG. 16 is an illustration of an alternative embodiment of the vacuum dressing, fully applied, where the vacuum dressing provides a flexible region for movement of a portion of a medical device without disturbing an established negative pressure environment over the insertion site of the medical device.

FIG. 16 illustrates an alternative embodiment of the inventive vacuum dressing, fully applied, where the vacuum dressing 1600 provides a flexible region 1611 for movement of a portion of a medical device 1601 without disturbing an established negative pressure environment over the insertion site of the medical device 1601. The dressing 1600 comprises a base dressing layer 1605 positioned beneath a portion of the medical device 1601, a top dressing layer 1610 positioned above a portion of the medical device 1601 and the insertion site, a sponge/foam member 1615, and vacuum tubing 1620. The flexible region 1611 is formed of applied dressing sections that attach to one another to maintain the vacuum seal under the top dressing layer 1610 and over the medical device 1601 insertion site, while permitting the portion of the medical device 1601 to move without disrupting the negative pressure environment applied over the insertion site of the medical device 1601.

Figure 17A:
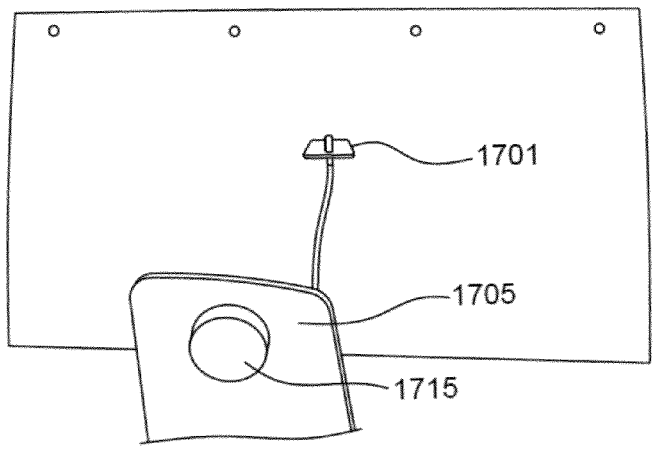
FIGS. 17A-F are illustrations of the steps of applying a third embodiment of the vacuum dressing, providing a flexible region for movement of a portion of a medical device without disturbing an established negative pressure environment over the insertion site of the medical device.
Figure 17B:
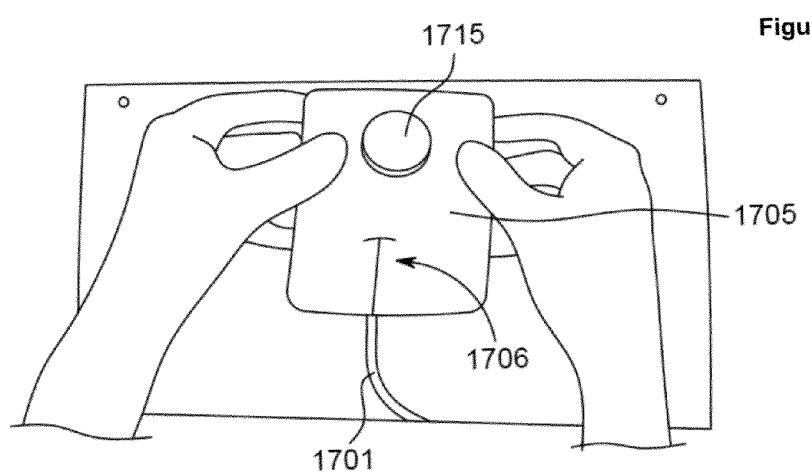
Figure 17C:
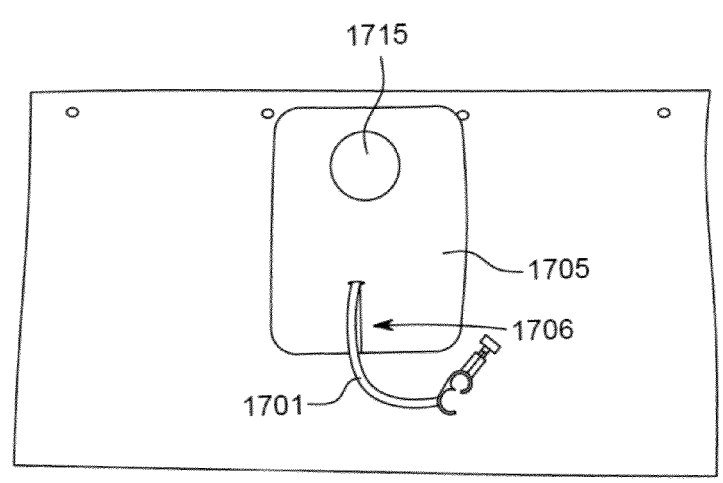

FIGS. 17A-F illustrate the steps of applying an alternative embodiment of the inventive vacuum dressing. In FIGS. 17A-C, a transparent thin film dressing 1705 having a slit 1706 therein is applied over the insertion site of a medical device 1701 (such as, but not limited to, a catheter). The dressing 1705 has a foam/sponge member 1715 disposed on the underside of the dressing 1705, such that the foam/sponge member 1715 is positioned over the insertion site. A portion of the medical device 1701 is disposed through the slit 1706, such that the portion of the medical device 1701 sits above the dressing 1705. In some embodiments, the portions of the dressing 1705 adjacent each other across the slit 1706 are overlapped to provide an airtight seal around the position where the medical device 1701 is disposed through the slit 1706.

Figure 17D:
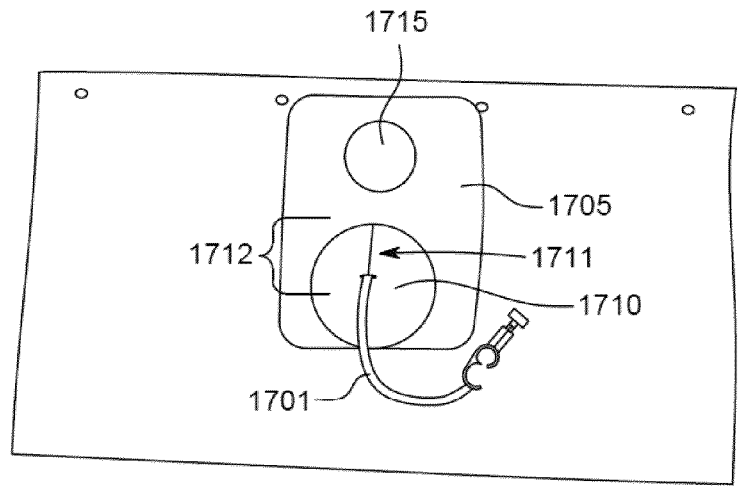
Figure 17E:
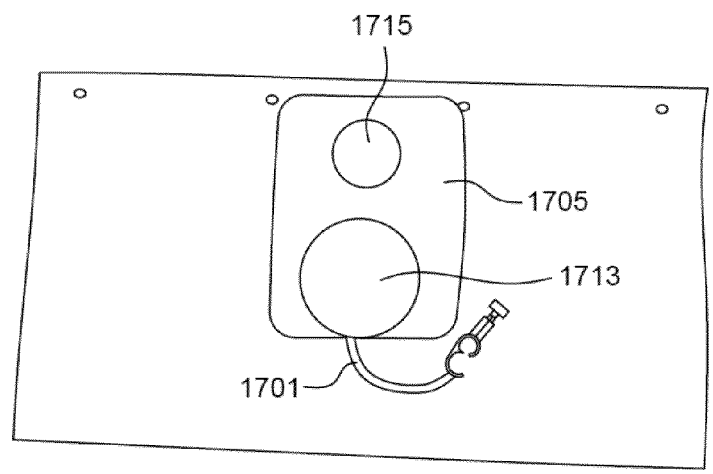
Figure 17F:
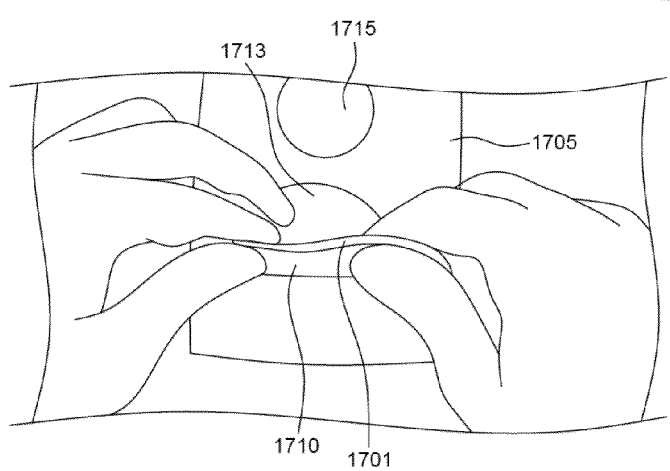

In FIG. 17D, a first thin film dressing closure member 1710 having a slit 1711 is applied with the portion of the medical device 1701 disposed through the slit 1711, such that the first closure member 1710 is beneath the portion of the medical device 1701. There is an adhesive region on the underside of the first closure member 1710 in the region 1712, above the terminal point of the slit 1711. In FIG. 17E, a second thin film dressing closure member 1713 is applied over the first closure member 1710 and the portion of the medical device 1701 on top of the first closure member 1710. As shown in FIG. 17F, the combination of 1) partial adhesion of the first closure member 1710 to the dressing member 1705 and 2) the second closure member 1713 on top of the first closure member 1710 provides an airtight seal around the portion of the medical device 1701, while also providing for movement of the portion of the medical device 1701 without disrupting a negative pressure environment applied over the insertion site of the medical device 1701 between the dressing 1700 and the patient's skin.

In an alternative embodiment, the first closure member 1710 does not have a slit, and a portion of the closure member 1710 is applied over the slit in the dressing 1705, providing a vacuum seal at the slit 1706. The remaining portion of the first closure member 1710 is folded back over itself, and the portion of the medical device 1701 sits on top of the folded over portion of the closure member 1710. The second closure member 1713 is then applied over the folded over portion of the first closure member 1710 and the portion of the medical device 1701 sitting thereon, as well as over a portion of the dressing 1705 and where the medical device 1701 is disposed therethrough. Thus, a flexible portion is formed, providing for movement of the portion of the medical device 1701 without disrupting a negative pressure environment applied over the insertion site of the medical device 1701 between the dressing 1700 and the patient's skin.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A vacuum dressing system for covering a medical device insertion site, comprising:
   a. a transparent film dressing member, comprising a body member having a slit adapted to permit a portion of a medical device to be disposed therethrough;
   b. a closure member adapted to adhere to the transparent film dressing member over the slit and beneath the portion of the medical device disposed through the slit to form a vacuum seal between the film dressing member and a region of skin surrounding the insertion site;
   c. a foam member coupled to the dressing member, adapted to be positioned over with the insertion site;
   d. a vacuum pressure source; and
   e. vacuum tubing, wherein the vacuum tubing permits negative pressure to be applied by the vacuum pressure source to the sealed region between the insertion site and the film dressing member;
   wherein the vacuum dressing system is adapted to provide a negative pressure environment over the insertion site and maintain the negative pressure environment despite movements of a portion of the medical device.

2. The vacuum dressing system of claim 1, wherein the closure member is a first flap extending from the transparent film dressing member and is adapted to fold over the slit and beneath the portion of the medical device disposed through the slit.

3. The vacuum dressing of claim 2, wherein the film dressing member further comprises a second flap adapted to fold over the first flap and over the portion of medical device disposed over the first flap, the second flap having a non-adhesive region in the area disposed over the portion of the medical device adapted to allow the vacuum dressing and the medical device to move independently of one another.

4. The vacuum dressing system of claim 1, wherein the foam member further comprises at least one of an antiseptic, antibiotic, and bacteriostatic agent.

5. The vacuum dressing system of claim 1, wherein the vacuum pressure source is at least one of a syringe or a mechanical non-electronic system that can apply and maintain a vacuum pressure.

6. The vacuum dressing system of claim 1, wherein the vacuum pressure source is an electronic vacuum pump.

7. The vacuum dressing system of claim 1, further comprising a sealable valve coupled to the vacuum tubing, to prevent back flow of air into the vacuum tubing when the vacuum pressure source is not attached to the vacuum tubing.

8. A method of using a vacuum dressing to cover a medical device insertion site, comprising:
   a. disposing the vacuum dressing over the medical device insertion site, wherein the vacuum dressing comprises a transparent film dressing, the transparent film dressing comprises a slit adapted to permit a portion of the medical device to be disposed therethrough and a closure member adapted to adhere to the transparent film dressing member over the slit and beneath the portion of the medical device disposed through the slit, a foam member comprising at least one of an antiseptic, antibiotic, or bacteriostatic agent, and vacuum tubing;
   b. sealing the transparent film dressing over and around the medical device insertion site; and
   c. applying a vacuum force through the vacuum tubing to a region around the medical device insertion site and sealed by the dressing, to obtain a desired vacuum level.

9. The method of claim 8, wherein the vacuum force creates an area of negative pressure around the medical device insertion site that will promote the fluids and possible infectious agents into the foam and away from the insertion site resulting in an anaerobic environment that inhibits the growth of aerobic infectious agents.

10. The method of claim 9, wherein a maintained vacuum level confirms that the dressing is providing anaerobic conditions and does not need to be changed.

11. The method of claim 9, further comprising the step wherein a loss of vacuum level indicates a need to reapply the vacuum force.

12. The method of claim 11, wherein failure to obtain the vacuum level by reapplying the vacuum force indicates a need to replace the dressing.

13. The method of claim 8, wherein the step of applying the vacuum force further comprises observing compression of the foam member in response to the applied vacuum force.

* * * * *